US008515688B2

(12) United States Patent
Wang et al.

(10) Patent No.: US 8,515,688 B2
(45) Date of Patent: Aug. 20, 2013

(54) SYSTEMS AND METHODS TO PREDICT FATIGUE LIVES OF ALUMINUM ALLOYS UNDER MULTIAXIAL LOADING

(75) Inventors: Qigui Wang, Rochester Hills, MI (US);
Yucong Wang, West Bloomfield, MI (US); Guoqiu He, Shanghai (CN); Chengshu Chen, Shanghai (CN); Zhengfei Hu, Shanghai (CN); Xiaoshan Liu, Shanghai (CN); Defeng Mo, Shanghai (CN)

(73) Assignee: GM Global Technology Operations LLC, Detroit, MI (US)

( * ) Notice: Subject to any disclaimer, the term of this patent is extended or adjusted under 35 U.S.C. 154(b) by 495 days.

(21) Appl. No.: 12/402,538

(22) Filed: Mar. 12, 2009

(65) Prior Publication Data
US 2010/0235110 A1  Sep. 16, 2010

(51) Int. Cl.
*G01B 5/30*  (2006.01)
*G06F 19/00*  (2011.01)

(52) U.S. Cl.
USPC .............. 702/35; 702/43; 702/181; 702/185; 703/2; 703/7

(58) Field of Classification Search
USPC ..................... 702/35, 185, 43, 181; 703/2, 7
See application file for complete search history.

(56) References Cited

U.S. PATENT DOCUMENTS

| | | | |
|---|---|---|---|
| 5,841,669 A * | 11/1998 | Purvis et al. | 702/179 |
| 7,623,973 B1 * | 11/2009 | Wang et al. | 702/34 |
| 7,889,840 B2 * | 2/2011 | Vasudevan et al. | 378/58 |
| 2008/0015827 A1 * | 1/2008 | Tryon et al. | 703/2 |
| 2009/0048788 A1 * | 2/2009 | Darehbidi et al. | 702/34 |
| 2010/0030537 A1 * | 2/2010 | Wang et al. | 703/5 |

FOREIGN PATENT DOCUMENTS
GB    2 223 855 A    4/1990

OTHER PUBLICATIONS

J. Coyne et al., "The effect of microstructure on the fatigue crack growth behaviour of an Al—Zn—Mg—(Zr) alloy", International Journal of Fracture, vol. 15, No. 5, Oct. 1979, p. 405-417.*
U. Kocabicak et al. "A simple approach for multiaxial fatigue damage prediction based on FEM post-processing", Materials and Design 25 (2004) 73-82, http://testfem.com/Journals/3_Journal.pdf.*

(Continued)

*Primary Examiner* — Michael Nghiem
*Assistant Examiner* — Alexander Satanovsky
(74) *Attorney, Agent, or Firm* — Dinsmore & Shohl LLP

(57) ABSTRACT

A system to predict a fatigue life of an aluminum alloy is disclosed herein. The system comprises a computer-readable medium cooperative with micromechanics-based fatigue life models for cyclic multiaxial loading. The fatigue life models predict the fatigue life by processing information received by the system relating to the aluminum alloy and the stress state present in the aluminum alloy. The received information comprises at least one of: a critical shear plane, a damage factor, a hardening factor defined by at least one of a plurality of uniaxial cyclic hardening factor parameters related to probabilistics of defects and microstructure characteristics in the aluminum alloy, an additional hardening factor related to non-proportionality, and thermophysical and mechanical properties of the aluminum alloy. The defects and microstructure characteristics can be calculated using mathematical modeling of casting, solidification and heat treatment processes or by an extreme value statistics based on metallography measurements.

26 Claims, 6 Drawing Sheets

(56) References Cited

OTHER PUBLICATIONS

Takamoto Itoh et al., "A damage model for estimating low cycle fatigue lives under nonproportional multiaxial loading", European Structural Integrity Society, vol. 31, 2003, pp. 423-439, http://www.sciencedirect.com/science/article/pii/S1566136903800237.*

Dariusz Rozumek, "Fatigue Crack Growth Rate In Aluminium Alloy Including Mixed Mode I and III", Journal of Theoretical and Applied Mechanics 43, 4, pp. 731-743, Warsaw 2005, http://www.ptmts.org.pl/rozumek-4-05.pdf.*

Nong Chen, "An Analytical Model Which Combines Roughness and Pasticity Induced Fatigue Crack Closure", Thesis, University of Illinois at Urna-Champaign, 1997, pp. 121, http://fcp.mechse.illinois.edu/reports/FCP_Report174.pdf.*

D.M. Li et al., "An Improvement on Prediction of Fatigue Crack Growth From Low Cycle Fatigue Properties", Engineering Fracture Mechanics vol. 60, No. 4, pp. 397-406, 1998, http://141.223.168.124/result/papers/int/35e.pdf.*

Strain-Life Fatigue Analysis, An EngineersToolbox, pp. 17, 2004— http://www.engrasp.com/doc/etb/mod/fm1/strainlife/strainlife_help.html.*

Y. Liu et al. "Strain-based multiaxial fatigue damage modeling", Fatigue Fract Engng Mater Struct 28, pp. 1177-1189.*

E.M. Viatkina et al. "Strain path dependency in metal plasticity", Netherlands Institute for Metals Research, Eindhoven University of Technology, Department of Mechanical Engineering, 2004, Section Dislocation cell structure', http://www.mate.tue.nl/mate/pdfs/3831.pdf.*

Dimitris Kosteas, "Fatigue Behaviour and Analysis", TALAT Lecture 2401, Technische Universität München, EAA—European Aluminium Association, 2004, 81 pp., http://core.materials.ac.uk/repository/eaa/talat/2401.pdf.*

Adila Afzal et al., "A Comparative Study of Fatigue Behavior and Life Predictions of Forged Steel and PM Connecting Rods", SAE International, 2003, 12 pp., http://www.mime.eng.utoledo.edu/faculty_staff/faculty/afatemi/papers/2004SAEAfzalFatemi2004-01-1529.pdf.*

De-Guang Shang et al., "A simple approach to the description of multiaxial cyclic stress relationship", International Journal of Fatigue, vol. 22, Issue 3, Mar. 2000, pp. 251-256.*

M. Bahmani et al., "The relationship between fatigue strength and microstructure in an austempered Cu—Ni—Mn—Mo alloyed ductile iron", Journal of Materials Science 32 (1997), pp. 5383-5388, http://www.springerlink.com/content/xu7008152342157g/fulltext.pdf.*

German Office Action dated Aug. 10, 2011 relating to German Application No. 10 2010 009 318.1.

* cited by examiner

SYSTEMS AND METHODS TO PREDICT FATIGUE LIVES OF ALUMINUM ALLOYS UNDER MULTIAXIAL LOADING

BACKGROUND

The present invention relates generally to the prediction of fatigue lives of aluminum alloys and, more particularly, to systems, methods, and articles of manufacture to predict fatigue lives of aluminum alloys under at least one of multiaxial proportional and non-proportional loading.

Fatigue life prediction of aluminum alloys, in particular, cast aluminum components, traditionally has been challenging not only because of microstructure complexity, but also because of uncertainty of defect population. Under multiaxial and, in particular, non-proportional loading, defects and microstructural discontinuities often play an important role in crack formation and fatigue properties. It is believed that the presence of defects and dislocation piling up and stacking near discontinuities may be attributed to local stress concentration and resultant fatigue crack initiation and propagation. The extent of the dislocation piling up and stacking near discontinuities may depend on not only a stress state present in the aluminum alloy, but also the loading path. Research has indicated that fatigue lives of aluminum alloys, such as 6063 and A356, under circular, non-proportional loading generally are much shorter than those under proportional loading with the same equivalent strain amplitude. The shorter fatigue lives may be due to maximum shear planes rotating and changing continuously during non-proportional loading. As a result, increasing numbers of dislocations are piled up and stacked near discontinuities during non-proportional loading, thereby, accelerating fatigue crack initiation and propagation and, thus, shortening the fatigue lives of aluminum alloys. As such, based on the foregoing, there exists a need for systems, methods, and articles of manufacture to accurately predict fatigue lives of aluminum alloys under multiaxial loading.

SUMMARY

It is against the above background that embodiments of the present invention provide systems, methods, and articles of manufacture to predict fatigue lives of aluminum alloys. More particularly, embodiments relate generally to systems, methods, and articles of manufacture that utilize micromechanics-based fatigue life models to predict fatigue lives of aluminum alloys. These fatigue life models may process information relating to aluminum alloys and the stress state present in the aluminum alloys to predict fatigue lives thereof. The information processed by the fatigue life models, and which generally is attributable to cyclic multiaxial non-proportional loading, may include, but is not necessarily limited to, at least one of: a critical shear plane of an aluminum alloy, a damage factor of an aluminum alloy, a hardening factor of an aluminum alloy, an additional hardening factor due to dislocation interactions in multiple slip systems, a microstructure characteristic value, and thermophysical and mechanical properties of an aluminum alloy. While the majority of the disclosure of the present application refers solely to non-proportional loading for simplification purposes, it is to be understood that this disclosure relates generally to the same extent and just as equally to proportional loading.

In accordance with one embodiment, a system to predict a fatigue life of an aluminum alloy under cyclic multiaxial loading comprises an information input, an information output, a processing unit, and a computer-readable medium. The information input is configured to receive at least one of information relating to the aluminum alloy and information relating to a stress state present in the aluminum alloy and microstructure characteristics and thermophysical and mechanical properties of the aluminum alloy. The information output is configured to convey information relating to the aluminum alloy. The computer-readable medium is cooperative with at least one micromechanics-based fatigue life model, wherein the fatigue life model predicts the fatigue life of the aluminum alloy by processing at least a portion of the received information. The received information comprises at least one of: a critical shear plane of the aluminum alloy where a shear strain amplitude is at its maximum value; a damage factor of the aluminum alloy, the damage factor defined by at least one of a plurality of damage factor parameters comprising a maximum shear strain amplitude, a normal strain amplitude, a maximum normal strain amplitude, a shear stress amplitude, and a normal stress amplitude; a hardening factor of the aluminum alloy, the hardening factor defined by at least one of a plurality of uniaxial cyclic hardening factor parameters comprising a fatigue strength coefficient, a fatigue ductility coefficient, a fatigue strength exponent, and a fatigue ductility exponent, wherein the uniaxial cyclic hardening factor parameters are related to probabilistics of defects and microstructure characteristics in the aluminum alloy; an additional hardening factor due to dislocation interactions in multiple slip systems, the additional hardening factor defined by at least one of an additional hardening coefficient, a hardening exponent of torsion, and a non-proportionality value, wherein at least one of the additional hardening coefficient, the hardening exponent of torsion, and the non-proportionality value is related to probabilistics of microstructure and dislocation structures in the aluminum alloy; and a microstructure characteristic and thermophysical and mechanical properties of the aluminum alloy defined by at least one of a defect size, a volume fraction of the defects, secondary dendrite arm spacing (SDAS), a grain size, a size of the second phase particle, an aspect ratio of the second phase particle, a volume fraction of the second phase particle, a shear modulus value, a Poisson ratio, and a Young's modulus value.

Optionally, the fatigue strength coefficient, $\sigma'_f$, of the uniaxial cyclic hardening parameters may be related to a size of the defect in the aluminum alloy. Based on liner elastic fracture mechanics (LEFM), the relationship between stress amplitude and fatigue life under uniaxial loading can be expressed as:

$$\frac{\Delta\sigma}{2} = \frac{1}{2} B^{\frac{1}{m}} \times a_i^{\frac{1}{m}-\frac{1}{2}} \times N_f^{-\frac{1}{m}} \quad (1)$$

where $a_i$ is the defect (such as pore or oxide inclusion) size; m is a fatigue crack growth Paris law exponent, which m may vary between about 3 to about 10 for cast aluminum alloys;

$$B = \left[\frac{m-2}{2} C_0 Y(a_i)^m U_R(a_i)^m \pi^{m/2}\right]^{-1};$$

and $Y(a_i)$ is the geometric correction factor. For the surface defect (crack) and interior defect (crack), $Y(a_i)$ may be taken to be about 0.65 and about 0.5, respectively. $U_R(a_i)$ is the crack closure factor. Where R=−1, the value of $U_R(a_i)$=0.5 simply assumes that the crack is fully open when normal stress becomes tensile. In high cycle fatigue, the relationship between stress amplitude and uniaxial fatigue life can be also expressed as:

$$\frac{\Delta\sigma}{2} = 2^{b_0}\sigma'_f N_f^{b_0} \quad (2)$$

where $b_0$ is the fatigue strength exponent. By comparing Equation (1) with Equation (2), the fatigue strength coefficient, $\sigma'_f$, may be a function of defect size ($a_i$) and expressed as:

$$\sigma'_f = F\left(a_i^{\frac{1}{m}-\frac{1}{2}}\right) \quad (3)$$

and the fatigue strength exponent $b_0$ can be a function of fatigue crack growth Paris law exponent and expressed as: $b_0 = F(-1/m)$. Also, the fatigue ductility coefficient, $\epsilon'_f$, of the uniaxial cyclic hardening parameters may be expressed as:

$$\epsilon'_f = \left(\frac{\sigma'_f}{k'}\right)^{c_0/b_0} = \left(\frac{\sigma'_f}{k'}\right)^{1/n'} = F\left(\frac{\sigma'_f}{k'}\right)^{1/n} \quad (4)$$

where k' and n' are the cyclic strength coefficient and the cyclic strain hardening exponent, respectively; n is the tensile strain hardening exponent that can be related to at least one of a volume fraction of defects, a volume fraction of second phase particles, and secondary dendrite arm spacing ((SDAS), a microstructure fineness measure) in the aluminum alloy and can be expressed as:

$$\sigma_{YS} + C_1(f_p - f_d)\alpha\epsilon^* + C_2(1 + (f_p - f_d)^{1/2})\left[\left(\frac{C_3}{L} + \frac{C_4}{\lambda}\right)(n - \epsilon^*)\right]^{1/2} = \frac{1}{2}C_2(1 + (f_p - f_d)^{1/2})\left(\frac{C_3}{L} + \frac{C_4}{\lambda}\right)^{1/2}(n - \epsilon^*)^{1/2} \quad (5)$$

where $\sigma_{YS}$ is the yield strength; $C_1$, $C_2$, $C_3$, $C_4$, and L are constants; and $\epsilon^*$ is the strain at the onset of plastic relaxation which, for cast Al—Si—Mg alloy, may be found by experiment to be about 0.007. $f_p$ and $f_d$ are volume fractions of second phase particles and defects, respectively; and, $\lambda$ is the secondary dendrite arm spacing (SDAS). Further, the fatigue ductility exponent, $c_0$, of the uniaxial cyclic hardening parameters also may be related to the tensile strain hardening exponent, n, and may be expressed as:

$$c_0 = \frac{b_0}{n'} = \frac{b_0}{F(n)}.$$

The tensile strain hardening exponent, n, can be calculated from Equation (5).

Further optionally, the fatigue life model may comprise a low cycle multiaxial fatigue life model. This low cycle multiaxial fatigue life model may be expressed as:

$$\frac{\Delta\gamma_{max}}{2} \cdot \frac{\Delta\tau}{2} + \frac{\Delta\epsilon_n}{2} \cdot \frac{\Delta\sigma_n}{2} = \quad (6)$$

-continued $$\left(\frac{3+v_e}{4}\right)\frac{\sigma'^2_f}{E}(2N_f)^{2b_0} + \left(\frac{3+v_p}{4}\right)\sigma'_f\epsilon'_f(2N_f)^{b_0+c_0}$$

where ($N_f$) is the fatigue life of the aluminum alloy; $\Delta\gamma_{max}$ is the maximum shear strain amplitude on the critical shear plane; $\Delta\tau$ is the shear stress amplitude on the critical shear plane; $\Delta\epsilon_n$ is the normal strain amplitude on the critical shear plane; $\Delta\sigma_n$ is the normal stress amplitude on the critical shear plane; $v_e$ and $v_p$ are the elastic and plastic Poisson ratios, respectively; E is the Young's modulus value; $\sigma'_f$ is the fatigue strength coefficient; $\epsilon'_f$ is the fatigue ductility coefficient; and $b_0$ and $c_0$ are the fatigue strength and the fatigue ductility exponents, respectively. The received information relating to the aluminum alloy further may comprise dislocation mobility that results in additional hardening of the aluminum alloy during cyclic multiaxial non-proportional loading. An additional hardening factor, due to the dislocation interactions in multiple slip systems activated by cyclic multiaxial non-proportional loading, may be defined by at least one of the additional hardening coefficient, the hardening exponent due to torsion, and the non-proportionality value. With the additional hardening factor, the low cycle fatigue life then can be predicted using just the maximum shear strain amplitude on the critical shear plane, $\Delta\gamma_{max}$; and normal strain amplitude on the critical shear plane, $\Delta\epsilon_n$. Here, the low cycle multiaxial fatigue life model may be expressed as:

$$\frac{\Delta\gamma_{max}}{2} + \frac{\Delta\epsilon_n}{2} = \left(\frac{3+v_e}{2}\right)\frac{\sigma'_f}{E}(2N_f)^{b_0} + \left(\frac{3+v_p}{2}\right)(1+L_0\Phi)^{\frac{-1}{n_0}}\epsilon'_f(2N_f)^{c_0} \quad (7)$$

where $L_0$ is the additional hardening coefficient under non-proportional loadings, which may vary between about 0.1 and about 0.15 for cast aluminum alloys; $n_0$ is the hardening exponent under torsion loading, which may equate to about 0.2~0.25 for cast aluminum alloys; and $\Phi$ is the non-proportionality value. When fatigue life under multiaxial proportional loading is being predicted, the non-proportionality value, $\Phi$, is equal to zero since non-proportionality is not of concern. When, however, fatigue life under multiaxial non-proportional loading is being predicted, the non-proportionality value, $\Phi$, may be expressed as:

$$\Phi = K_c\frac{\overline{S_{np}}^{-1/2} - \overline{S_p}^{-1/2}}{\overline{S_c}^{-1/2} - \overline{S_p}^{-1/2}} = K_c\frac{(\overline{S_{np}}/\overline{S_p})^{-1/2} - 1}{(\overline{S_c}/\overline{S_p})^{-1/2} - 1} \quad (8)$$

where $K_c$ is a constant and $\overline{S_p}$, $\overline{S_c}$, $\overline{S_{np}}$ are statistical mean free sliding distances of dislocations in the aluminum alloy under proportional, circle, and other non-proportional loading paths, respectively.

Further, optionally, the fatigue life model may comprise a high cycle multiaxial fatigue life model that may be expressed as:

$$\frac{\Delta\gamma_{max}}{2} + \frac{\Delta\epsilon_{max}}{2} = (2+v_e)\frac{\sigma'_f}{E}(2N_f)^{b_0} + (1+L_0\Phi)^{\frac{-1}{n_0}}(2+v_p)\epsilon'_f(2N_f)^{c_0} \quad (9)$$

where $\Delta\epsilon_{max}$ is the maximum normal strain amplitude on the critical shear plane. Again, when fatigue life under multiaxial proportional loading is being predicted, the non-proportionality value, $\Phi$, is equal to zero since non-proportionality is not of concern. When, however, fatigue life under multiaxial non-proportional loading is being predicted, the non-proportionality value, $\Phi$, may expressed as, and determined according to, Equation (8) above.

In accordance with another embodiment, a method of predicting a fatigue life of an aluminum alloy under cyclic multiaxial loading comprises configuring a computer-based system to predict the fatigue life. The computer-based system comprises an information input, an information output, at least one of an information memory and an instruction-storing memory, a central processing unit, and computer-readable program code means to process at least a portion of the information received by the information input. The method further comprises predicting the fatigue life of the aluminum alloy with the computer-based system according to processes of the computer-readable program code means.

In accordance with another embodiment, an article of manufacture to predict a fatigue life of an aluminum alloy under cyclic multiaxial loading comprises a computer-based system to predict the fatigue life. The computer-based system comprises an information input, an information output, at least one of an information memory and an instruction-storing memory, a central processing unit, and computer-readable program code means to process at least a portion of the information received by the information input. The computer-based system predicts the fatigue life of the aluminum alloy according to processes of the computer-readable program code means.

BRIEF DESCRIPTION OF THE DRAWINGS

The following detailed description of specific embodiments can be best understood when read in conjunction with the following drawings, where like structure is indicated with like reference numerals and in which.

Figure 1:
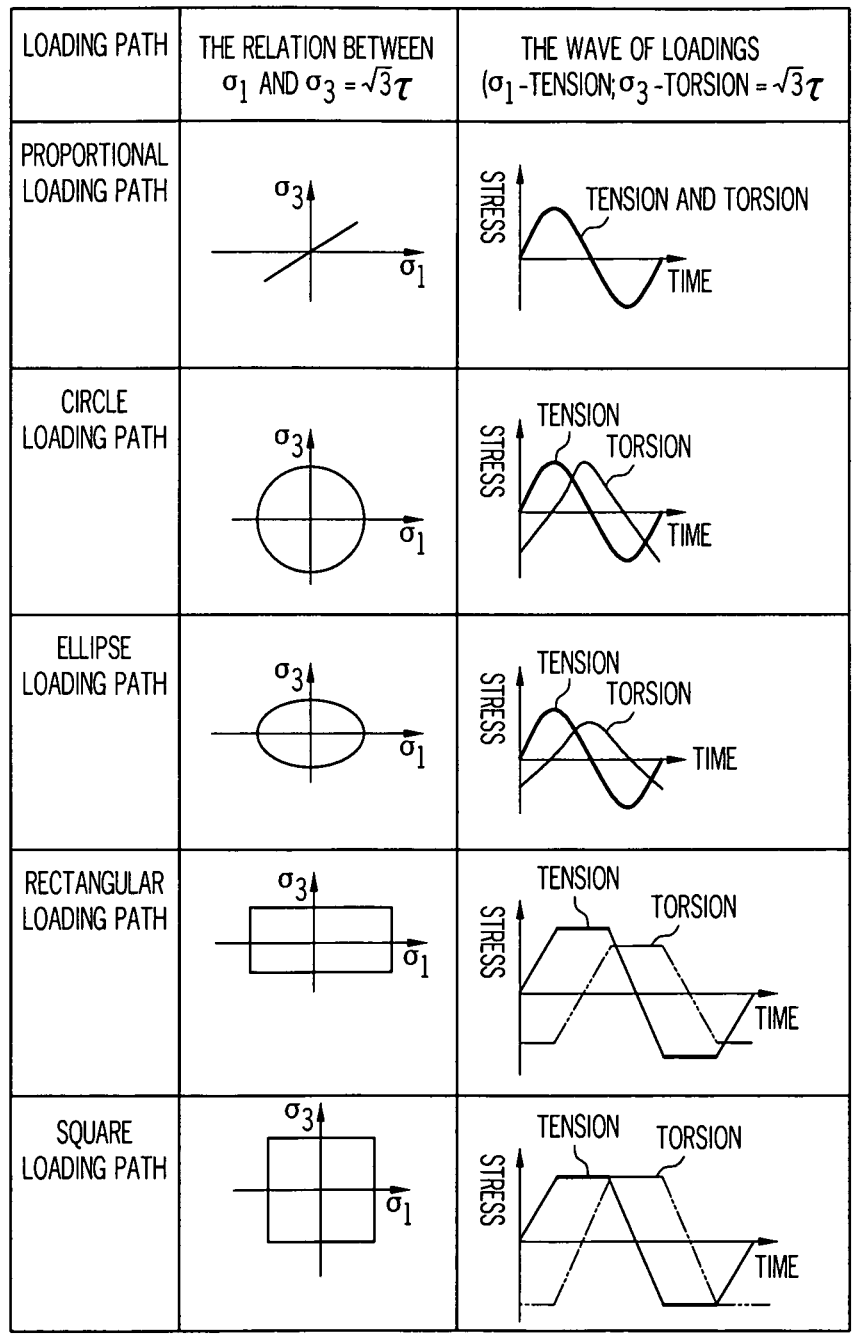
FIG. 1 is a chart illustrating tension and torsion stresses and their respective loading waveforms in both proportional and non-proportional loading paths.

The embodiments set forth in the drawings are illustrative in nature and are not intended to be limiting of the embodiments defined by the claims. Moreover, individual aspects of the drawings and the embodiments will be more fully apparent and understood in view of the detailed description that follows.

DETAILED DESCRIPTION

Embodiments of the present invention relate generally to systems, methods, and articles of manufacture to predict fatigue lives of aluminum alloys under cyclic multiaxial loading. As mentioned above, fatigue life under at least one of multiaxial proportional and non-proportional loading may be predicted using an embodiment of the present invention. As such, it is contemplated that embodiments may be operable to predict fatigue lives of aluminum alloys under either multiaxial proportional or non-proportional loading, or both.

Embodiments respectively comprise and/or utilize at least, but not limited to, one micromechanics-based fatigue life model to process at least one of information relating to an aluminum alloy and information relating to a stress state present in the aluminum alloy to predict a fatigue life of the aluminum alloy. As used herein, "aluminum alloy" refers not only to an alloy itself, but also to any part, product, and/or component at least partially configured of an aluminum alloy. Further, as used herein, "micromechanics" refers generally to an analysis of a multi-component (chemical elements) alloy and/or material on the level of one or more individual phases that cumulatively constitute an alloy or composite. As such, the micromechanics-based fatigue life models described herein consider probabilistics of defects and microstructure characteristics in the aluminum alloy when predicting a fatigue life of the aluminum alloy under multiaxial loading thereof.

Further, as used herein, "proportional" refers generally to loading paths when the principal strain axes of an aluminum alloy under multiaxial loading are substantially consistent and unchanging and, as used herein, "non-proportional" refers generally to loading paths when the principal strain axes of an aluminum alloy during cyclic multiaxial loading are continuously rotating and changing and, thus, are not proportional. An example of non-proportional loading is an aluminum alloy bar subjected to alternating cycles of tension and torsion loading. In this example, between the tension and torsion cycles, the principal strain axis rotates about 45°. Out-of-phase loading is a form of non-proportional loading and is used to denote cyclic loading histories with sinusoidal or triangular waveforms and a phase difference between the loads. FIG. 1 lists exemplary relationships between tensile and torsion stresses and their respective loading waveforms under different loading paths.

Figure 2A:
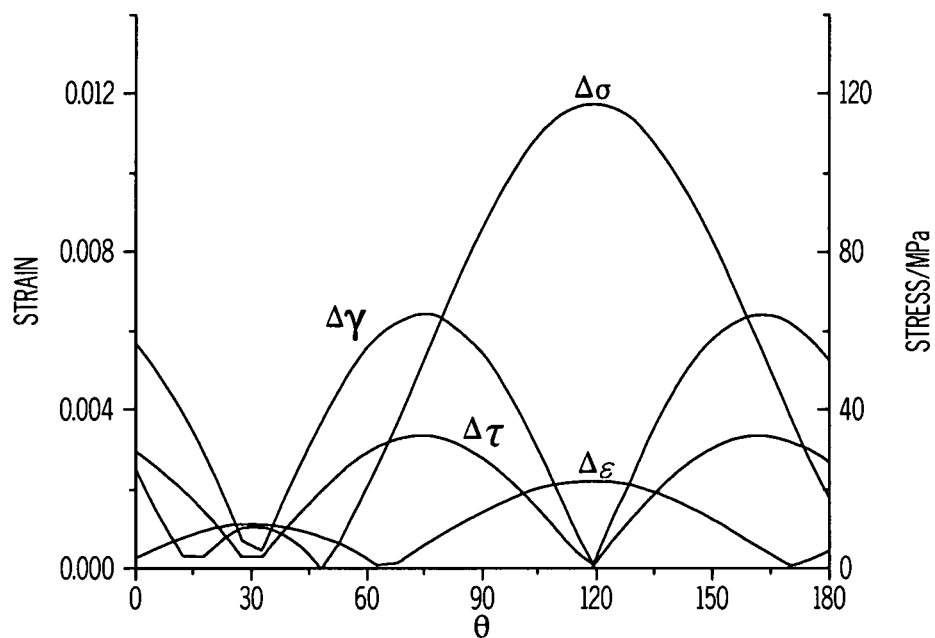
FIG. 2A is a graphical illustration of stress and strain states on a critical plane of an aluminum alloy under proportional loading.
Figure 2B:
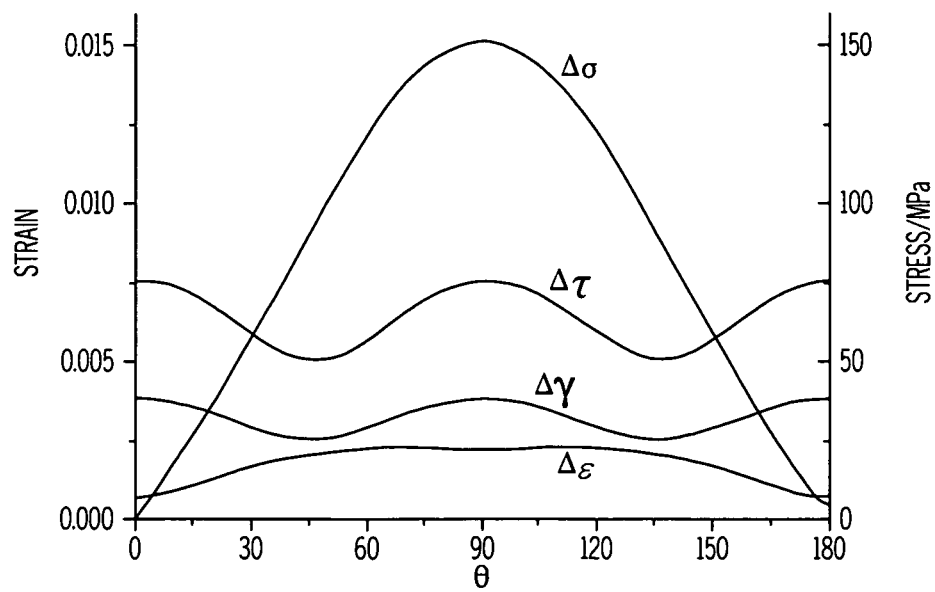
FIG. 2B is a graphical illustration of stress and strain states on a critical plane of an aluminum alloy under non-proportional loading.

FIG. 2 graphically illustrates an example of stress and strain state on a critical plane of an A356 aluminum alloy subjected to a equivalent strain amplitude of $\Delta\epsilon_{eq}/2=0.22\%$. In the plots shown in FIGS. 2A and 2B, the respective shear and normal stress and strain amplitudes on a critical plane, which, for example, is perpendicular to the cylindrical surface of a thin-wall pipe specimen, are shown as functions of angles between the critical plane and the axis of the cylindrical specimen. Under proportional loading (FIG. 2A), the shear stress amplitude $\Delta\tau$ and shear strain amplitude $\Delta\gamma$ on the critical plane are out of phase with the normal stress amplitude $\Delta\sigma$ and normal strain amplitude $\Delta\epsilon$. Thus, for example, as shown in FIG. 2A, when the normal stress amplitude $\Delta\sigma$ and normal strain amplitude $\Delta\epsilon$ are at their respective maximum values, the shear stress amplitude $\Delta\tau$ and shear strain amplitude $\Delta\gamma$ are not at their respective maximum values and, in fact, typically are at or near their respective minimum values. Thus, it also follows that, when the shear stress amplitude $\Delta\tau$ and shear strain amplitude $\Delta\gamma$ are at their respective maximum values, the normal stress amplitude $\Delta\sigma$ and normal strain amplitude $\Delta\epsilon$ are not at their respective maximum values and, in fact, typically are at or near their respective minimum values.

Under non-proportional loading (FIG. 2B), however, the shear stress amplitude $\Delta\tau$ and shear strain amplitude $\Delta\gamma$ on the critical plane are in phase and concurrent, or substantially concurrent, with the normal stress amplitude $\Delta\sigma$ and normal strain amplitude $\Delta\epsilon$. Thus, the shear stress amplitude $\Delta\tau$ and shear strain amplitude $\Delta\gamma$ are at or near their respective maximum values when the normal stress amplitude $\Delta\sigma$ and normal strain amplitude $\Delta\epsilon$ are at their respective maximum values and vice versa. Thus, it also follows that the shear stress amplitude $\Delta\tau$ and shear strain amplitude $\Delta\gamma$ are at or near their respective minimum values when the normal stress amplitude $\Delta\sigma$ and normal strain amplitude $\Delta\epsilon$ are at their respective minimum values and vice versa. The in phase and concurrent maximization, or approximate maximization, of both the shear stress and stain amplitudes and the normal stress and strain amplitudes promotes fatigue crack initiation and propagation in the aluminum alloy. As such, aluminum alloys under proportional loading typically have longer fatigue lives than aluminum alloys under non-proportional loading with the same equivalent strain amplitude as that of the proportional loading.

Figure 3:
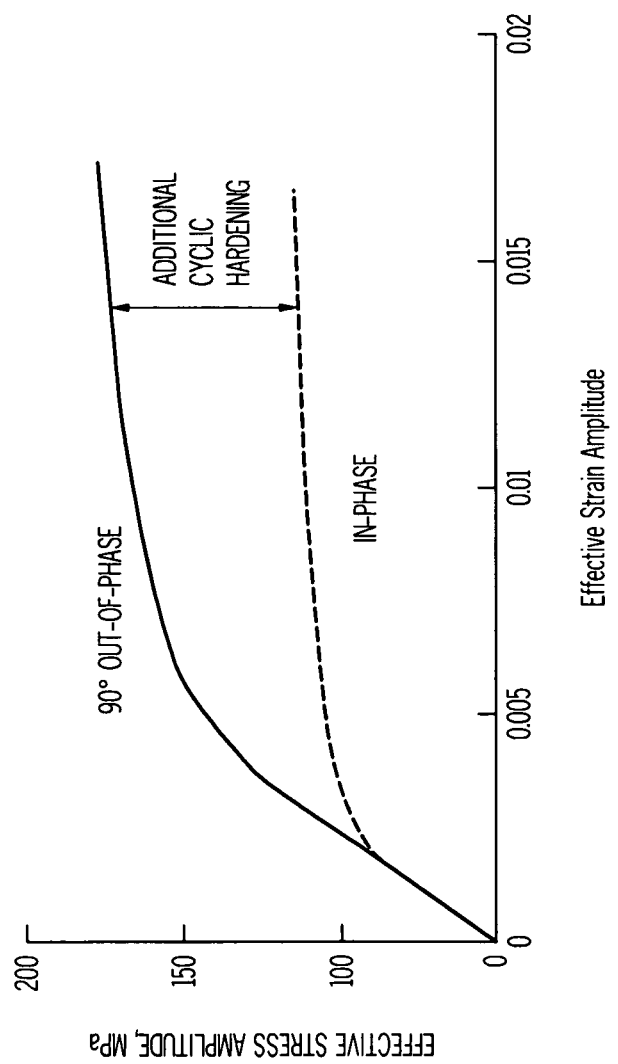
FIG. 3 is a graphical illustration of additional hardening observed in an aluminum alloy under non-proportional loading.

An additional hardening occurs during this type of non-proportional loading. Such additional hardening typically is not found in uniaxial or any proportional loading path. FIG. 3 graphically illustrates an example of converted effective stresses and strains under a non-proportional loading path with 90° out-of-phase tension-torsion loading. The 90° out-of-phase loading path has been found to produce the largest degree of non-proportional additional hardening. The magnitude of the additional hardening observed for this loading path, as compared to that observed in uniaxial or proportional loading, generally is highly dependent on the microstructure characteristics and the ease with which slip systems develop in a material. In aluminum alloys, for instance, the circle loading path has been found to produce the maximum additional hardening among several 90° out-of-phase loading paths evaluated.

The shortened fatigue lives of aluminum alloys can be problematic for a number reasons dependent on the applications of the alloys. For example, in the automotive industry, failure of aluminum automotive components may increase warranty costs and may negatively impact the quality and performance of the component. Embodiments of the present invention are operable to predict fatigue lives of aluminum alloys during their development stages and prior to their applications and, as such, may eliminate such problems or minimize their effects. In addition, embodiments of the present invention may significantly reduce aluminum component development and observation/testing cycles traditionally necessary to measure fatigue life.

Figure 4:
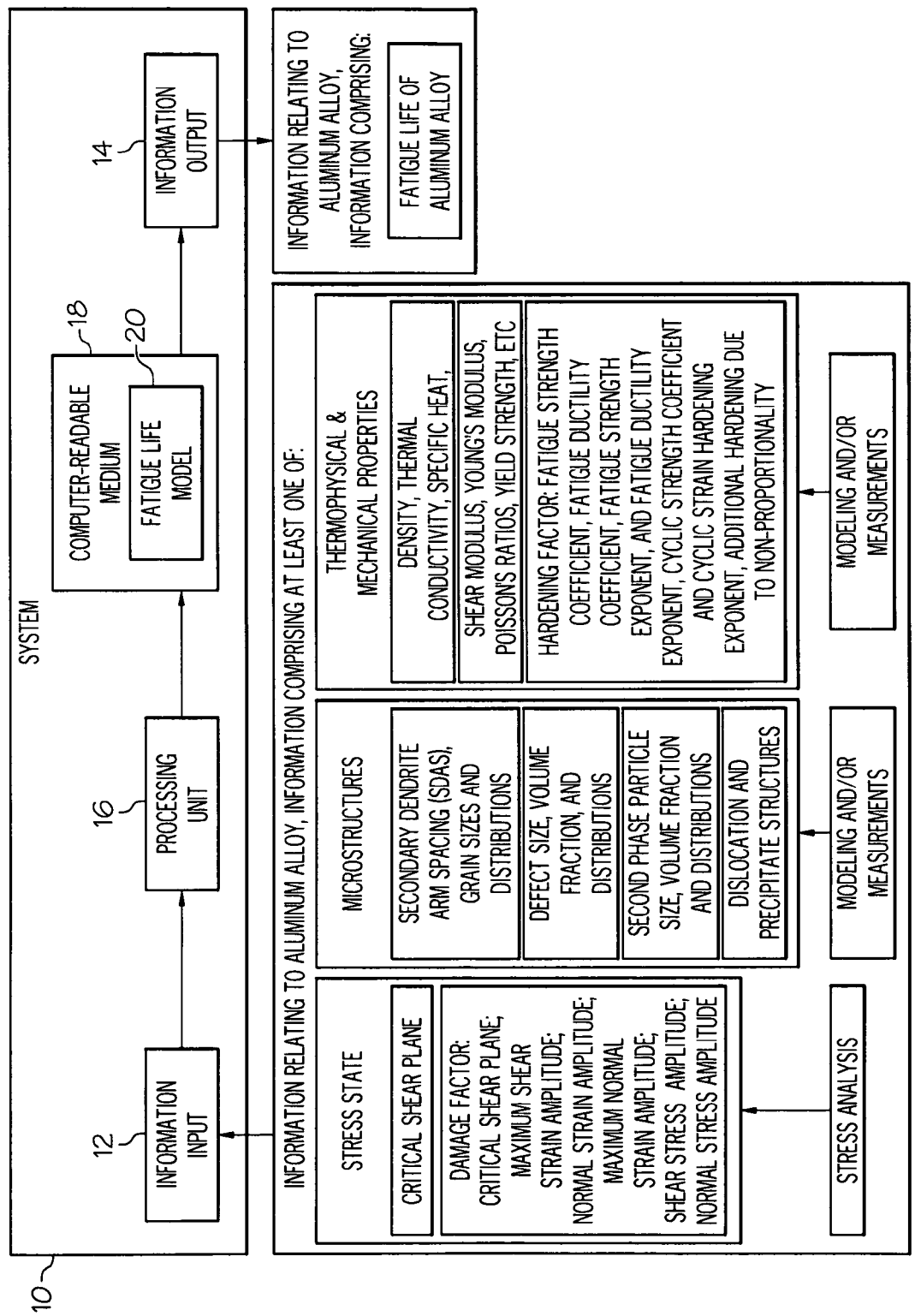
FIG. 4 is a block diagram of a system to predict a fatigue life of an aluminum alloy according to one embodiment of the present invention.

In one embodiment, presented in a block diagram in FIG. 4, a system 10 to predict a fatigue life of an aluminum alloy under cyclic multiaxial loading comprises an information input 12, an information output 14, a processing unit 16, a computer-readable medium 18, and at least one micromechanics-based fatigue life model 20. The information input 12 is configured to receive at least one of information relating to the aluminum alloy and information relating to a stress state present in the aluminum alloy, this information cumulatively referred to herein as "received information". The information output 14 is configured to convey information relating to the aluminum alloy. The computer-readable medium 18 is cooperative with the micromechanics-based fatigue life model 20 to predict the fatigue life of the aluminum alloy by processing the received information. The information relating to the aluminum alloy conveyed by the information output 14 comprises the fatigue life of the aluminum alloy predicted by the fatigue life model 20. The processing unit 16 may be a central processing unit that may interpret instructions inputted to the system 10, a data processing unit that may translate data or other information or convert data to another data form, or other processing unit. It is contemplated that the information input 12, information output 14, processing unit 16, and computer-readable medium 18 may comprise or be provided as any conventional information input, information output, processing unit, and computer-readable medium known in the art operable to perform as described herein. Further, it is contemplated that the system 10 described herein may be a computer-based system or other machine-based or implemented system operable to perform as described herein.

The information received by the information input relating to the stress state present in the aluminum alloy comprises at least one of: a critical shear plane of the aluminum alloy and a damage factor of the aluminum alloy. The critical shear plane of the aluminum alloy is where a shear strain amplitude is at its maximum value. The critical shear plane may be, for example, perpendicular to a cylindrical surface of a thin-walled pipe specimen. The damage factor of the aluminum alloy is attributable to the cyclic multiaxial loading. The damage factor is defined by at least one of a plurality of damage factor parameters comprising a maximum shear strain amplitude $\Delta\gamma_{max}$, a shear stress amplitude $\Delta\tau$, a maximum normal strain amplitude $\Delta\epsilon_{max}$, a normal strain amplitude $\Delta\epsilon_n$, and a normal stress amplitude $\Delta\sigma_n$.

The hardening factor of the aluminum alloy also is attributable to cyclic multiaxial loading. The hardening factor is defined by at least one of a plurality of uniaxial cyclic hardening factor parameters. The uniaxial cyclic hardening factor parameters are related to probabilistics of defects and microstructure characteristics in the aluminum alloy. The uniaxial cyclic hardening factor parameters may be determined through strain-life low cycle uniaxial fatigue testing. In one embodiment, the uniaxial cyclic hardening factor parameters comprise a fatigue strength coefficient $\sigma'_f$, a fatigue ductility coefficient $\epsilon'_f$, a fatigue strength exponent $b_0$, and a fatigue ductility exponent $c_0$. The fatigue strength coefficient, $\sigma'_f$, of the uniaxial cyclic hardening parameters may be related to a size of the defect in the aluminum alloy.

When based on liner elastic fracture mechanics (LEFM), the relationship between stress amplitude and fatigue life under uniaxial loading can be expressed as:

$$\frac{\Delta\sigma}{2} = \frac{1}{2} B^{\frac{1}{m}} \times a_i^{\frac{1}{m}-\frac{1}{2}} \times N_f^{-\frac{1}{m}} \tag{10}$$

where $a_i$ is the defect (such as, for example, pore or oxide inclusion) size; m is the fatigue crack growth Paris law exponent, which may vary from about 3 to about 10 for cast aluminum alloys;

$$B = \left[\frac{m-2}{2}C_0 Y(a_i)^m U_R(a_i)^m \pi^{m/2}\right]^{-1};$$

and $Y(a_i)$ is the geometric correction factor. For the surface defect (crack) and interior defect (crack), $Y(a_i)$ may be taken to be about 0.65 and about 0.5, respectively. $U_R(a_i)$ is the crack closure factor. Where $R=-1$, the value of $U_R(a_i)=0.5$ may simply assume that the crack is fully open when normal stress becomes tensile. In high cycle fatigue, the relationship between stress amplitude and uniaxial fatigue life can be also expressed as:

$$\frac{\Delta\sigma}{2} = 2^{b_0}\sigma'_f N_f^{b_0} \quad (11)$$

where $b_0$ is the fatigue strength exponent. By comparing Equations (10) and (11), the fatigue strength coefficient, $\sigma'_f$, may be a function of defect size and expressed as:

$$\sigma'_f = F\left(a_i^{\frac{1}{m}-\frac{1}{2}}\right) \quad (12)$$

The fatigue strength exponent $b_0$ may be a function of fatigue crack growth Paris law exponent and expressed as: $b_0 = F(-1/m)$. Also, the fatigue ductility coefficient, $\epsilon'_f$, of the uniaxial cyclic hardening parameters may be expressed as:

$$\varepsilon'_f = \left(\frac{\sigma'_f}{k'}\right)^{c_0/b_0} = \left(\frac{\sigma'_f}{k'}\right)^{1/n'} = F\left(\frac{\sigma'_f}{k'}\right)^{1/n} \quad (13)$$

where k' and n' are the cyclic strength coefficient and the cyclic strain hardening exponent, respectively; n is the tensile strain hardening exponent that can be related to at least one of: a volume fraction of defects, a volume fraction of second phase particles, and secondary dendrite arm spacing (SDAS), a microstructure fineness measure) in the aluminum alloy. n may be expressed as:

$$\sigma_{YS} + C_1(f_p - f_d)\alpha\varepsilon^* + C_2(1+(f_p-f_d)^{1/2})\left[\left(\frac{C_3}{L}+\frac{C_4}{\lambda}\right)(n-\varepsilon^*)\right]^{1/2} = \quad (14)$$
$$\frac{1}{2}C_2(1+(f_p-f_d)^{1/2})\left(\frac{C_3}{L}+\frac{C_4}{\lambda}\right)^{1/2}(n-\varepsilon^*)^{1/2}$$

where $\sigma_{YS}$ is the yield strength; $C_1$, $C_2$, $C_3$, $C_4$, and L are constants; and $\epsilon^*$ is the strain at the onset of plastic relaxation, which, for cast Al—Si—Mg alloy, may be found by experiment to be about 0.007. $f_p$ and $f_d$ are volume fractions of second phase particles and defects, respectively; and $\lambda$ is the secondary dendrite arm spacing (SDAS). Further, the fatigue ductility exponent, $c_0$, of the uniaxial cyclic hardening factor parameters also may be related to the tensile strain hardening exponent (n) and may be expressed as:

$$c_0 = \frac{b_0}{n'} = \frac{b_0}{F(n)}.$$

The tensile strain hardening exponent, n, can be calculated from Equation (14). Further, in another embodiment, the information received by the information input may include microstructure characteristics and thermophysical and mechanical properties and may comprise at least one of: secondary dendrite arm spacing (SDAS), a grain size, a second phase particle size, an aspect ratio of second phase particles, a defect size, a volume fraction of defects, a volume fraction of the second phase particles, and a shear modulus value. Further, the received information, in addition to or in the alternative to the above, may comprise at least one of, a Poisson ratio, a Young's modulus value, and an additional hardening factor of the aluminum alloy attributable to additional damage to the aluminum alloy under cyclic multiaxial non-proportional loading. More particularly, the additional hardening factor considers the influence of non-proportionality in plastic deformation and, thus, fatigue crack initiation and propagation. As such, the additional hardening factor due to dislocation interactions in multiple slip systems activated by cyclic multiaxial non-proportional loading is defined by at least one of: an additional hardening coefficient under non-proportional loading ($L_0$), a hardening exponent under torsion loading ($n_0$); and a non-proportionality value ($\Phi$). For example, for cast aluminum alloys, the additional hardening coefficient ($L_0$) generally is between about 0.1 and about 0.15 and the hardening exponent under torsion ($n_0$) generally varies from between about 0.2 and about 0.25; Further, the non-proportionality value ($\Phi$) may be expressed as:

$$\Phi = K_c \frac{\overline{S_{np}}^{-1/2} - \overline{S_p}^{-1/2}}{\overline{S_c}^{-1/2} - \overline{S_p}^{-1/2}} = K_c \frac{(\overline{S_{np}}/\overline{S_p})^{-1/2} - 1}{(\overline{S_c}/\overline{S_p})^{-1/2} - 1} \quad (15)$$

where $K_c$ is a constant and $\overline{S}_p$, $\overline{S}_c$, $\overline{S}_{np}$ are statistical mean free sliding distances of dislocations in the aluminum alloy under proportional, circle, and other non-proportional loading paths, respectively. Thus, the non-proportionality value is defined as a mean value of free sliding distances of dislocations, which may vary according to the loading path, as shown in Table 1. It should be noted that "non-proportional", as used herein, refers to loading paths such as, circle, diamond, square, rectangle, ellipse loading paths, presented in Table 1, and other loading paths that are not proportionally directed to the aluminum alloy. Further, as indicated in Table 1, when a fatigue life is being predicted under multiaxial proportional loading, the non-proportionality value, $\Phi$, equals zero since non-proportionality is a non-factor and is not of concern. When, however, a fatigue life is being predicted under multiaxial non-proportional loading, the non-proportionality value, $\Phi$, may be expressed, and determined with Equation (15).

TABLE 1

Non-proportionality values under different loading paths.

| | Loading Path | | | | | |
|---|---|---|---|---|---|---|
| | Circle | Diamond | Square | Rectangle | Ellipse | Proportional |
| Non-proportionality ($\Phi$) | 0.75 | 0.675 | 0.67 | 0.60 | 0.50 | 0 |

Further, the information received by the information input may relate to detailed microstructure characteristics of the aluminum alloy that may be provided using parameters related to multi-scale mathematical modeling of casting, solidification, and heat treatment processes. The mean values of the microstructure characteristics, for instance, a mean size of pores or second phase particles, are calculated based on nominal baseline of the alloy composition, casting, solidification, and heat treatment process parameters. The probabilistics of the microstructure characteristics may be dependent upon statistical variations of alloy compositions, casting, solidification, and heat treatment process parameters.

The information received by the information input relating to the microstructures characteristics of the aluminum alloy can be provided by various means of measurements including conventional two-dimensional metallographic measurements. Metallographic techniques are widely utilized in practice to characterize casting defects and microstructure characteristics in two dimensions (2D). With the conventional 2D metallographic data, the size distributions of casting defects and other microstructure characteristics can be described by a extreme value statistics (EVS) with a cumulative distribution function such as:

$$F(x) = \exp\left(-\exp\left(-\frac{x-\zeta}{\delta}\right)\right) \quad (16)$$

where x is the characteristic parameter of casting defects or microstructure characteristics, and $\zeta$ and $\delta$ are referred to as the extreme value statistical distribution parameters. It is contemplated that Equation (16) is merely exemplary of such functions, and other similar distribution functions can be used to fit the experimental data.

The micromechanics-based fatigue life model predicts the fatigue life of the aluminum alloy by processing at least a portion of the information received by the information input. In one embodiment, the fatigue life model comprises a low cycle multiaxial fatigue life model. As used herein, "low cycle" refers to when the fatigue life ($N_f$) of an aluminum alloy is less than $10^4$ cycles ($N_f < 10^4$ cycles). One embodiment of a low cycle multiaxial fatigue life model may be expressed as:

$$\frac{\Delta\gamma_{max}}{2} \cdot \frac{\Delta\tau}{2} + \frac{\Delta\varepsilon_n}{2} \cdot \frac{\Delta\sigma_n}{2} = \quad (17)$$

$$\left(\frac{3+v_e}{4}\right)\frac{\sigma'^2_f}{E}(2N_f)^{2b_0} + \left(\frac{3+v_p}{4}\right)\sigma'_f\varepsilon'_f(2N_f)^{b_0+c_0}$$

The low cycle multiaxial fatigue life model of Equation (17) may predict a fatigue life ($N_f$) of an aluminum alloy when the maximum shear strain amplitude ($\Delta\gamma_{max}$), the shear stress amplitude ($\Delta\tau$), the normal strain amplitude ($\Delta\varepsilon_n$), and the normal stress amplitude ($\Delta\sigma_n$) and their constitutive relationships on the critical shear plane are known.

Figure 5:
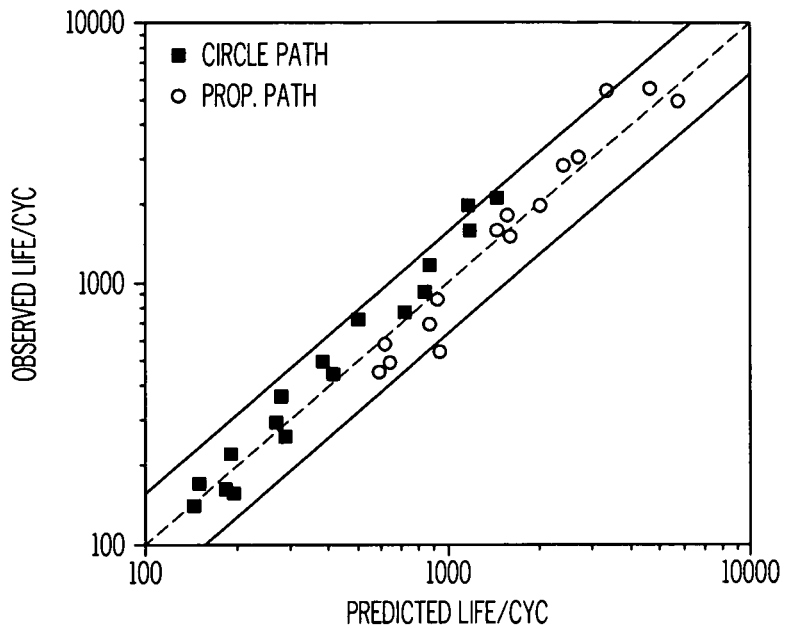
FIG. 5 is a graphical illustration of a comparison between observed low cycle multiaxial fatigue lives for a cast aluminum alloy and low cycle multiaxial fatigue lives for the same alloy predicted according to another embodiment of the present invention.

FIG. 5 graphically illustrates an exemplary comparison of low cycle multiaxial fatigue lives of a cast A356 aluminum alloy observed using conventional fatigue life measuring methodologies, including, but not necessarily limited to, observation of physical fatigue testing, and low cycle multiaxial fatigue lives of the same alloy predicted using the low cycle multiaxial fatigue life model of Equation (17). Here, the Young's modulus value is 74 GPa and the uniaxial cyclic hardening factor parameters are given as follows: $\sigma'_f=360$ MPa, $b_0=-0.125$, $\varepsilon'_f=0.12$, $c_0=-0.61$. For A356 aluminum alloy, the elastic Poisson ratio ($v_e$) is 0.3 and the plastic Poisson ratio ($v_p$) is 0.5. The comparison of FIG. 5 reveals that the fatigue lives predicted using the low cycle multiaxial fatigue life model of Equation (17) are in substantial agreement with the observed fatigue lives with nearly all of the plotted fatigue life points being within 1.5 times scatter band for both proportional and circle, i.e., non-proportional, loading paths.

Another embodiment of the low cycle multiaxial fatigue life model may be expressed as:

$$\frac{\Delta\gamma_{max}}{2} + \frac{\Delta\varepsilon_n}{2} = \quad (18)$$

$$\left(\frac{3+v_e}{2}\right)\frac{\sigma'_f}{E}(2N_f)^{b_0} + \left(\frac{3+v_p}{2}\right)(1+L_0\Phi)^{\frac{-1}{n_0}}\varepsilon'_f(2N_f)^{c_0}$$

The low cycle multiaxial fatigue life model of Equation (18) may predict a fatigue life ($N_f$) of an aluminum alloy when one or more of the maximum shear strain amplitude ($\Delta\gamma_{max}$), the shear stress amplitude ($\Delta\tau$), the normal strain amplitude ($\Delta\varepsilon_n$), and the normal stress amplitude ($\Delta\sigma_n$) and their constitutive relationships on the critical shear plane are not known. Further, a comparison of Equation (17) and Equation (18) reveals that, while Equation (18) simplifies the stress and strain processes of Equation (17), Equation (18) considers the influence of non-proportionality on the aluminum alloy by processing the additional hardening factor due to dislocation interactions in multiple slip systems (i.e., at least one of the hardening coefficient under non-proportional loading ($L_0$), the hardening exponent under torsion loading ($n_0$), and the non-proportionality value ($\Phi$)), which is not taken into consideration by Equation (17).

Figure 6:
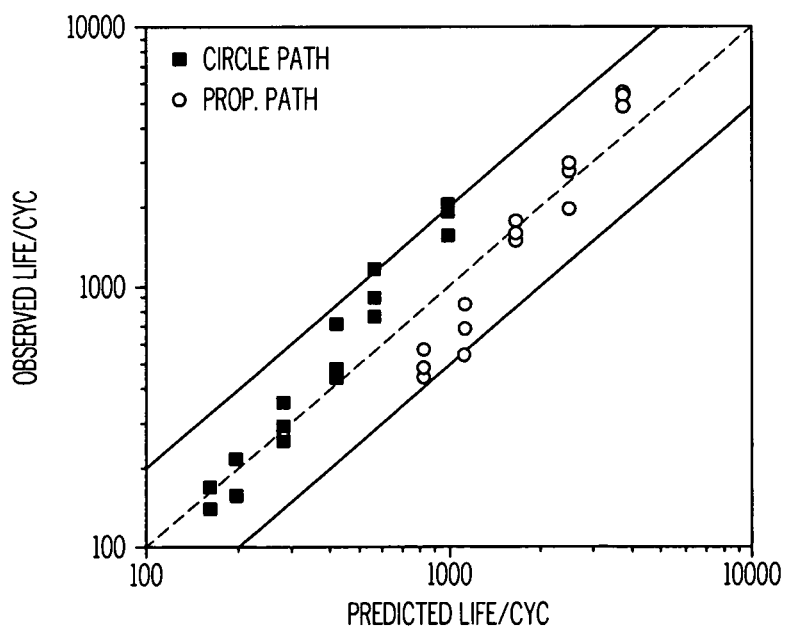
FIG. 6 is a graphical illustration of a comparison between observed low cycle multiaxial fatigue lives for a cast aluminum alloy and low cycle multiaxial fatigue lives for the same alloy predicted according to another embodiment of the present invention.

FIG. 6 graphically illustrates an exemplary comparison of observed low cycle multiaxial fatigue lives of a cast A356 aluminum alloy and low cycle multiaxial fatigue lives of the same alloy predicted using the low cycle multiaxial fatigue life model of Equation (18). Here, the Young's modulus value (E) is 74 GPa and the uniaxial cyclic hardening factor parameters are given as follows: $\sigma'_f=360$ MPa, $b_0=-0.125$, $\varepsilon'_f=0.12$, $c_0=-0.61$. For A356 aluminum alloy, the elastic Poisson ratio ($v_e$) is 0.3 and the plastic Poisson ratio ($v_p$) is 0.5. The hardening coefficient under non-proportional loading ($L_0$) is 0.141 and the hardening exponent under torsion loading ($n_0$) is 0.22. The comparison of FIG. 6 reveals that while the accuracy of the fatigue lives predicted by Equation (18) with the observed fatigue lives is slightly lower than the accuracy provided by Equation (17), there remains significant agreement between the fatigue lives predicted by Equation (18) and the observed fatigue lives with nearly all of the plotted fatigue life points being within 2 times scatter band for both proportional and circle, i.e., non-proportional, loading paths with consideration of the influence of non-proportionality.

In another embodiment of the micromechanics-based fatigue life model, the fatigue life model comprises a high cycle multiaxial fatigue life model. As used herein, "high cycle" refers to when the fatigue life ($N_f$) of an aluminum alloy is greater than $10^4$ cycles ($N_f > 10^4$ cycles). In high cycle fatigue regimes, the applied stress on the aluminum alloy usually is low and, as such, the length of time prior to initiation of fatigue cracks can be substantially long. For example, in metallic materials, the length of time prior to fatigue crack initiation can be as long as 90% of the material's total fatigue life. Further, under multiaxial loading, the driving force for fatigue crack initiation generally is directly related to the maximum normal strain on the critical shear plane.

In one embodiment, the high cycle multiaxial fatigue life model for aluminum alloys under multiaxial non-proportional loading is expressed as:

$$\frac{\Delta\gamma_{max}}{2} + \frac{\Delta\varepsilon_{max}}{2} = (2+v_e)\frac{\sigma'_f}{E}(2N_f)^{b_0} + (1+L_0\Phi)^{\frac{-1}{n_0}}(2+v_p)\varepsilon'_f(2N_f)^{c_0} \quad (19)$$

where $\Delta\varepsilon_{max}$ is the maximum normal strain amplitude. Equation (19) is specific to application to high cycle regimes, while Equations (17) and (18) are specific to application to low cycle regimes. Further, Equation (19) simplifies the stress and strain processes of Equation (17), but considers the influence of non-proportionality on the aluminum alloy by processing the additional hardening factor due to dislocation interactions in multiple slip systems, which is not taken into consideration by Equation (17).

Figure 7:
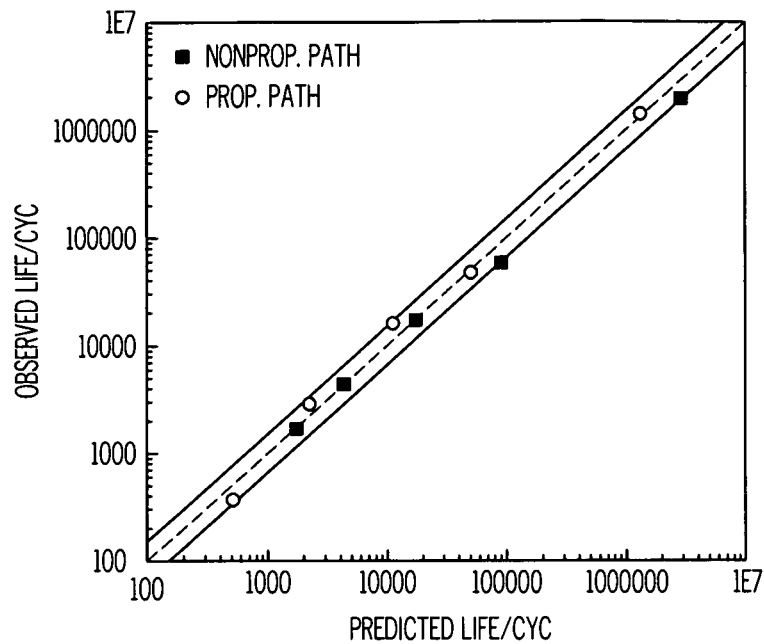
FIG. 7 is a graphical illustration of a comparison between observed high cycle multiaxial fatigue lives for an aluminum alloy and high cycle multiaxial fatigue lives for the same alloy predicted according to another embodiment of the present invention.

Table 2 and FIG. 7 provide an exemplary comparison of observed high cycle multiaxial fatigue lives of a 6063 aluminum alloy. More particularly, FIG. 7 graphically illustrates an exemplary comparison of observed high cycle multiaxial fatigue lives of a 6063 aluminum alloy and high cycle multiaxial fatigue lives of the same alloy predicted using the high cycle multiaxial fatigue life model of Equation (19). Here, the Young's modulus value (E) is 68 GPa and the uniaxial cyclic hardening factor parameters are given as follows: $\sigma'_f$=411 MPa, $b_0$=-0.1, $\varepsilon'_f$=0.2, $c_0$=-0.67. For the 6063 aluminum alloy, the elastic Poisson ratio ($v_e$) is 0.3 and the plastic Poisson ratio ($v_p$) is 0.5. The additional hardening coefficient under non-proportional loading ($L_0$) is 0.11 and the hardening exponent under torsion loading ($n_0$) is 0.2. The comparison of FIG. 7 reveals that the fatigue lives predicted using the high cycle multiaxial fatigue life model of Equation (19) are in substantial agreement with the observed fatigue lives with nearly all of the plotted fatigue life points being within 1.5 times scatter band for both proportional and non-proportional loading paths.

Table 2 provides an exemplary comparison of observed high cycle multiaxial fatigue lives and predicted high cycle multiaxial fatigue lives (using the fatigue life model of Equation (19)) of a 6063 aluminum alloy under different non-proportional loading paths.

TABLE 2

A comparison of predicted and observed fatigue lives of a 6063 aluminum alloy under different non-proportional loading paths.

| Loading path | Non-proportionality Φ | Observed fatigue life | Predicted fatigue life | Ratio of predicted/observed fatigue life |
|---|---|---|---|---|
| Ellipse | 0.5 | 1.3 × 10⁵ | 1.8 × 10⁵ | 1.38 |
| Rectangle | 0.6 | 8.1 × 10⁴ | 1.0 × 10⁵ | 1.23 |
| Square | 0.67 | 6.8 × 10⁴ | 4.0 × 10⁴ | 0.59 |

Figure 8:
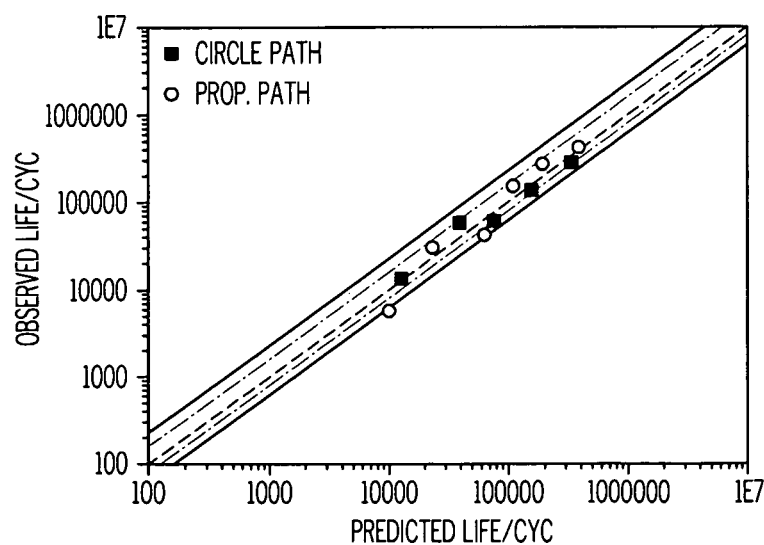
FIG. 8 is a graphical illustration of a comparison between observed high cycle multiaxial fatigue lives for a hipped cast aluminum alloy and high cycle multiaxial fatigue lives for the same alloy predicted according to another embodiment of the present invention.

FIG. 8, meanwhile, graphically illustrates an exemplary comparison of observed high cycle multiaxial fatigue lives of a cast A356-T6 (hot isostatic pressed, hipped) aluminum alloy and high cycle multiaxial fatigue lives of the same alloy predicted using the high cycle multiaxial fatigue life model of Equation (19). Here, the Young's modulus value (E) is 74 GPa and the uniaxial cyclic hardening factor parameters are given as follows: $\sigma'_f$=587 MPa, $b_0$=-0.124, $\varepsilon'_f$=0.011, $c_0$=-0.511. For the cast A356-T6 (hipped) aluminum alloy, the elastic Poisson ratio ($v_e$) is 0.3 and the plastic Poisson ratio ($v_p$) is 0.5. The additional hardening coefficient under non-proportional loading ($L_0$) is 0.11 and the hardening exponent under torsion loading ($n_0$) is 0.2. The comparison of FIG. 8 reveals that, in considering the presence of both the maximum shear strain amplitude and the maximum normal strain amplitude on the critical plane, the fatigue lives predicted using the high cycle multiaxial fatigue life model of Equation (19) are in substantial agreement with the observed fatigue lives with nearly all of the plotted fatigue life points being within 2 times scatter band for both proportional and circle, i.e., non-proportional, loading paths.

Additional embodiments of the present invention relate generally to methods of predicting fatigue lives of aluminum alloys under cyclic multiaxial non-proportional loading. In one embodiment, a method comprises configuring a computer-based system to predict the fatigue life of an aluminum alloy. The computer-based system comprises: an information input configured to receive at least one of information relating to the aluminum alloy and information relating to a stress state present in the aluminum alloy, an information output configured to convey information relating to the aluminum alloy, at least one of an information memory (e.g., random-access memory (RAM)) and an instruction-storing memory (e.g., read-only memory (ROM)), a central processing unit, and computer-readable program code means to process at least a portion of the received information relating to the aluminum alloy and the stress state present in the aluminum alloy.

The received information of the information input relating to the stress state in the aluminum alloy comprises at least one of: a critical shear plane of the aluminum alloy where a shear strain amplitude is at its maximum value; a damage factor of the aluminum alloy attributable to cyclic multiaxial loading, the damage factor defined by at least one of a plurality of damage factor parameters comprising a maximum shear strain amplitude, a normal strain amplitude, a maximum normal strain amplitude, a shear stress amplitude, and a normal stress amplitude. The received information relating to the aluminum alloy includes microstructure characteristics and thermophysical and mechanical properties and comprises at least one of: secondary dendrite arm spacing (SDAS); a grain size; a defect size; a volume fraction of defects; a size of the second phase particle; an aspect ratio of second phase particles; a volume fraction of the second phase particles; a shear modulus value; a Poisson ratio; and a Young's modulus value; a hardening factor of the aluminum alloy attributable to cyclic multiaxial loading, the hardening factor defined by at least one of a plurality of uniaxial cyclic hardening factor parameters comprising a fatigue strength coefficient, a fatigue ductility coefficient, a fatigue strength exponent, and a fatigue ductility exponent; and an additional hardening factor due to dislocation interactions in multiple slip systems activated by cyclic multiaxial non-proportional loading, the additional hardening factor defined by at least one of: an additional hardening coefficient, a hardening exponent of torsion, and a non-proportionality value. The uniaxial cyclic hardening factor parameters of the hardening factor may be related to probabilistics of defects and microstructure characteristics in the aluminum alloy.

The method further comprises predicting the fatigue life of the aluminum alloy with the computer-based system according to processes of the computer-readable program code means. In one embodiment, the computer-readable program code means comprise a low cycle multiaxial fatigue life model, while in another embodiment, the computer-readable program code means comprise a high cycle multiaxial fatigue life model. In yet another embodiment, the computer-readable program code means comprise both a low cycle multiaxial fatigue life model and a high cycle multiaxial fatigue life model.

Further, additional embodiments of the present invention relate generally to articles of manufacture respectively comprising a computer-usable medium comprising computer-readable program code means embedded therein to predict a fatigue life of an aluminum alloy under cyclic multiaxial loading. It is contemplated that fatigue lives under either or both of multiaxial proportional and non-proportional loading may be predicted by the computer-readable program code means. In one embodiment, the computer-readable program code means in the article of manufacture comprise at least one of: computer-readable program code means for processing a critical shear plane of the aluminum alloy where a shear strain amplitude is at its maximum value; computer-readable program code means for processing a damage factor of the aluminum alloy attributable to cyclic multiaxial loading, the damage factor defined by at least one of a plurality of damage factor parameters comprising a maximum shear strain amplitude, a normal strain amplitude, a maximum normal strain amplitude, a shear stress amplitude, and a normal stress amplitude; computer-readable program code means for processing a hardening factor of the aluminum alloy attributable to cyclic multiaxial loading, the hardening factor defined by at least one of a plurality of uniaxial cyclic hardening factor parameters comprising a fatigue strength coefficient, a fatigue ductility coefficient, a fatigue strength exponent, and a fatigue ductility exponent; and computer-readable program code means for processing an additional hardening factor of the aluminum alloy attributable to cyclic multiaxial non-proportional loading, the additional hardening factor defined by at least one of an additional hardening coefficient, a hardening exponent of torsion, and a non-proportionality value; computer-readable program code means for processing the received information relating to the aluminum alloy including microstructural, thermophysical, and mechanical properties and comprising at least one of: secondary dendrite arm spacing; a grain size; a defect size; a volume fraction of defects; a size of the second phase particle; an aspect ratio of the second phase particles; a volume fraction of the second phase particles; a shear modulus value; a Poisson ratio; and a Young's modulus value. In one embodiment, the computer-readable program code means are operable in low cycle regimes, while in another embodiment, the computer-readable program code means are operable in high cycle regimes. In yet another embodiment, the computer-readable program code means are operable in both low cycle and high cycle regimes.

Based on the foregoing, it is contemplated that the micromechanics-based fatigue life model may comprise at least one of, and/or any combination of, the low cycle multiaxial fatigue life model of Equation (17), the low cycle multiaxial fatigue life model of Equation (18), and the high cycle multiaxial fatigue life model of Equation (19). Thus, embodiments of the present invention may be operable in low cycle regimes, high cycle regimes, and/or both low and high cycle regimes to predict fatigue lives of aluminum alloys. Further, while the aluminum alloys of A356, 6063, and A356-T6 (hipped) are evaluated herein for exemplary purposes, it is contemplated that embodiments of the present invention may be operable to predict fatigue lives of one or more of any types of aluminum alloys.

It is noted that recitations herein of a component of an embodiment being "configured" in a particular way or to embody a particular property, or function in a particular manner, are structural recitations as opposed to recitations of intended use. More specifically, the references herein to the manner in which a component is "configured" denotes an existing physical condition of the component and, as such, is to be taken as a definite recitation of the structural factors of the component.

It is noted that terms like "generally," "commonly," and "typically," when utilized herein, are not utilized to limit the scope of the claimed embodiments or to imply that certain features are critical, essential, or even important to the structure or function of the claimed embodiments. Rather, these terms are merely intended to identify particular aspects of an embodiment or to emphasize alternative or additional features that may or may not be utilized in a particular embodiment.

For the purposes of describing and defining embodiments herein it is noted that the terms "substantially," "significantly," and "approximately" are utilized herein to represent the inherent degree of uncertainty that may be attributed to any quantitative comparison, value, measurement, or other representation. The terms "substantially," "significantly," and "approximately" are also utilized herein to represent the degree by which a quantitative representation may vary from a stated reference without resulting in a change in the basic function of the subject matter at issue.

Having described embodiments of the present invention in detail, and by reference to specific embodiments thereof, it will be apparent that modifications and variations are possible without departing from the scope of the embodiments defined in the appended claims. More specifically, although some aspects of embodiments of the present invention are identified herein as preferred or particularly advantageous, it is contemplated that the embodiments of the present invention are not necessarily limited to these preferred aspects.

What is claimed is:

1. A system to predict a fatigue life of an aluminum alloy under cyclic multiaxial loading, the system comprising:
   an information input configured to receive at least one of information relating to the aluminum alloy and information relating to a stress state present in the aluminum alloy and microstructure characteristics and thermophysical and mechanical properties of the aluminum alloy;
   an information output configured to convey information relating to the aluminum alloy;
   a processing unit; and
   a computer-readable medium cooperative with at least one micromechanics-based fatigue life model program which is stored thereon, wherein the fatigue life model predicts the fatigue life of the aluminum alloy by processing the received information, the received information comprising:
      a hardening factor of the aluminum alloy, the hardening factor defined by at least one of a plurality of uniaxial cyclic hardening factor parameters comprising a fatigue strength coefficient, a fatigue ductility coefficient, a fatigue strength exponent, and a fatigue ductility exponent, wherein the uniaxial cyclic hardening factor parameters are related to probabilistics of defects and microstructure characteristics in the aluminum alloy,
      an additional hardening factor due to dislocation interactions in multiple slip systems, the additional hardening factor defined by at least one of an additional hardening coefficient, a hardening exponent of torsion, and a non-proportionality value, wherein at least one of the additional hardening coefficient, the hardening exponent of torsion, and the non-proportionality value is related to probabilistics of microstructure and dislocation structures in the aluminum alloy, and at least one of:
   a critical shear plane of the aluminum alloy where a shear strain amplitude is at its maximum value,
   a damage factor of the aluminum alloy, the damage factor defined by at least one of a plurality of damage factor parameters comprising a maximum shear strain amplitude, a normal strain amplitude, a maximum normal strain amplitude, a shear stress amplitude, and a normal stress amplitude,
a microstructure characteristic and thermophysical and mechanical properties of the aluminum alloy defined by at least one of a defect size, a volume fraction of the defects, secondary dendrite arm spacing (SDAS), a grain size, a size of the second phase particle, an aspect ratio of the second phase particle, a volume fraction of the second phase particle, a shear modulus value, a Poisson ratio, and a Young's modulus value and;
   wherein size distributions of casting defects or microstructure characteristics are determined by an extreme value statistics (EVS) with a cumulative distribution function expressed as:

$$F(x) = \exp\left(-\exp\left(-\frac{x-\zeta}{\delta}\right)\right)$$

where x is a characteristic parameter of casting defects or microstructure characteristics and $\zeta$ and $\delta$ are extreme value statistical distribution parameters.

2. The system of claim 1, wherein at least one of the plurality of uniaxial cyclic hardening factors is the fatigue strength coefficient, and wherein the fatigue strength coefficient ($\sigma'_f$) is related to the defect size ($a_i$) in the aluminum alloy through an inverse of a fatigue crack growth Paris law exponent (m).

3. The system of claim 1, wherein at least one of the plurality of uniaxial cyclic hardening factors is the fatigue strength exponent, and wherein the fatigue strength exponent ($b_0$) is inversely related to a fatigue crack growth Paris law exponent (m).

4. The system of claim 1, wherein at least one of the plurality of uniaxial cyclic hardening factors is the fatigue ductility exponent, and wherein the fatigue ductility exponent ($c_0$) is proportionally related to the fatigue strength exponent ($b_0$) and inversely related to a tensile strain hardening exponent (n).

5. The system of claim 1, wherein:
the microstructure characteristics of the aluminum alloy are provided using one or more parameters related to a multi-scale mathematical modeling of casting, solidification, and heat treatment processes,
the mean values of the microstructure characteristics are calculated based on a nominal baseline of the casting, solidification, and heat treatment process parameters of the aluminum alloy, and
the probabilistics of the microstructure characteristics is dependent upon statistical variations of the casting, solidification, and heat treatment process parameters of the aluminum alloy.

6. The system of claim 1, wherein at least one of the plurality of uniaxial cyclic hardening factors is the fatigue ductility coefficient, and wherein the fatigue ductility coefficient ($\epsilon'_f$) is related to the ratio of fatigue strength coefficient ($\sigma'_f$) to the cyclic strength coefficient (k') through an inverse of a tensile strain hardening exponent (n).

7. The system of claim 6, wherein the tensile strain hardening exponent (n) is related to at least one of a volume fraction of defects, a volume fraction of second phase particles, secondary dendrite arm spacing (SDAS), and the yield strength of the aluminum alloy and is expressed as:

$$\sigma_{YS} + C_1(f_p - f_d)\alpha\varepsilon^* + C_2(1+(f_p-f_d)^{1/2})\left[\left(\frac{C_3}{L}+\frac{C_4}{\lambda}\right)(n-\varepsilon^*)\right]^{1/2} = \frac{1}{2}C_2(1+(f_p-f_d)^{1/2})\left(\frac{C_3}{L}+\frac{C_4}{\lambda}\right)^{1/2}(n-\varepsilon^*)^{1/2}$$

where $\sigma_{YS}$ is a yield strength, $C_1$, $C_2$, $C_3$, $C_4$, and L are constants, $\epsilon^*$ is a strain at the onset of plastic relaxation, $f_p$ and $f_d$ are volume fractions of second phase particles and defects, respectively, and $\lambda$ is a secondary dendrite arm spacing (SDAS).

8. The system of claim 1, wherein the fatigue life model comprises a low cycle multiaxial fatigue life model.

9. The system of claim 8, wherein the low cycle multiaxial fatigue life model is expressed as:

$$\frac{\Delta\gamma_{max}}{2}\cdot\frac{\Delta\tau}{2}+\frac{\Delta\epsilon_n}{2}\cdot\frac{\Delta\sigma_n}{2} = \left(\frac{3+v_e}{4}\right)\frac{\sigma'^2_f}{E}(2N_f)^{2b_0}+\left(\frac{3+v_p}{4}\right)\sigma'_f\epsilon'_f(2N_f)^{b_0+c_0}$$

where ($N_f$) is the fatigue life of the aluminum alloy; $\Delta\gamma_{max}$ is the maximum shear strain amplitude on the critical shear plane; $\Delta\tau$ is the shear stress amplitude on the critical shear plane; $\Delta\epsilon_n$ is the normal strain amplitude on the critical shear plane; $\Delta\sigma_n$ is the normal stress amplitude on the critical shear plane; $v_e$ and $v_p$ are the elastic and plastic Poisson ratios, respectively; E is the Young's modulus value; $\sigma'_f$ is the fatigue strength coefficient; $\epsilon'_f$ is the fatigue ductility coefficient; and $b_0$ and $c_0$ are the fatigue strength and the fatigue ductility exponents, respectively.

10. The system of claim 8, wherein the low cycle multiaxial fatigue life model is expressed as:

$$\frac{\Delta\gamma_{max}}{2}+\frac{\Delta\epsilon_n}{2} = \left(\frac{3+v_e}{2}\right)\frac{\sigma'_f}{E}(2N_f)^{b_0}+\left(\frac{3+v_p}{2}\right)(1+L_0\Phi)^{\frac{-1}{n_0}}\epsilon'_f(2N_f)^{c_0}$$

where ($N_f$) is the fatigue life of the material; $\Delta\gamma_{max}$ is the maximum shear strain amplitude on the critical shear plane; $\Delta\epsilon_n$ is the normal strain amplitude on the critical shear plane; $v_e$ and $v_p$ are the elastic and plastic Poisson ratios, respectively; E is the Young's modulus value; $\sigma'_f$ is the fatigue strength coefficient; $\epsilon'_f$ is the fatigue ductility coefficient; $b_0$ and $c_0$ are the fatigue strength and the fatigue ductility exponents, respectively; $L_0$ is the additional hardening coefficient under non-proportional loadings; $n_0$ is the hardening exponent under torsion loading; and $\Phi$ is the non-proportionality value.

11. The system of claim 10, wherein the low cycle multiaxial fatigue life model predicts the fatigue life of the aluminum alloy under multiaxial proportional loading and the non-proportionality value, $\Phi$, equals zero.

12. The system of claim 10, wherein the low cycle multiaxial fatigue life model predicts the fatigue life of the aluminum alloy under multiaxial non-proportional loading and the non-proportionality value, $\Phi$, is expressed as:

$$\Phi = K_c \frac{\overline{S_{np}}^{-1/2} - \overline{S_p}^{-1/2}}{\overline{S_c}^{-1/2} - \overline{S_p}^{-1/2}} = K_c \frac{(\overline{S_{np}}/\overline{S_p})^{-1/2} - 1}{(\overline{S_c}/\overline{S_p})^{-1/2} - 1}$$

where $K_c$ is a constant and $\overline{S_p}$, $\overline{S_c}$, $\overline{S_{np}}$ are statistical mean free sliding distances of dislocations in the aluminum alloy under proportional, circle, and other non-proportional loading paths, respectively.

13. The system of claim 10, wherein the additional hardening coefficient, $L_0$ varies between about 0.1 and about 0.15 and the hardening exponent under torsion ($n_0$) varies between about 0.2 and about 0.25.

14. The system of claim 1, wherein the fatigue life model comprises a high cycle multiaxial fatigue life model.

15. The system of claim 14, wherein the high cycle multiaxial fatigue life model is expressed as:

$$\frac{\Delta\gamma_{max}}{2} + \frac{\Delta\varepsilon_{max}}{2} = (2+v_e)\frac{\sigma'_f}{E}(2N_f)^{b_0} + (1+L_0\Phi)^{\frac{-1}{n_0}}(2+v_p)\varepsilon'_f(2N_f)^{c_0}$$

where ($N_f$) is the fatigue life of the aluminum alloy; $\Delta\gamma_{max}$ is the maximum shear strain amplitude on the critical shear plane; $\Delta\varepsilon_{max}$ is the maximum normal strain amplitude on the critical shear plane; $v_e$ and $v_p$ are the elastic and plastic Poisson ratios, respectively; E is the Young's modulus value; $\sigma'_f$ is the fatigue strength coefficient; $\varepsilon'_f$ is the fatigue ductility coefficient; $b_0$ and $c_0$ are the fatigue strength and the fatigue ductility exponents, respectively; $L_0$ is the additional hardening coefficient under non-proportional loadings; $n_0$ is the hardening exponent under torsion loading; and $\Phi$ is the non-proportionality value.

16. The system of claim 15, wherein the high cycle multiaxial fatigue life model predicts the fatigue life of the aluminum alloy under multiaxial proportional loading and the non-proportionality value, $\Phi$, equals zero.

17. The system of claim 15, wherein the high cycle multiaxial fatigue life model predicts the fatigue life of the aluminum alloy under multiaxial non-proportional loading and the non-proportionality value, $\Phi$, is expressed as:

$$\Phi = K_c \frac{\overline{S_{np}}^{-1/2} - \overline{S_p}^{-1/2}}{\overline{S_c}^{-1/2} - \overline{S_p}^{-1/2}} = K_c \frac{(\overline{S_{np}}/\overline{S_p})^{-1/2} - 1}{(\overline{S_c}/\overline{S_p})^{-1/2} - 1}$$

where $K_c$ is a constant and $\overline{S_p}$, $\overline{S_c}$, $\overline{S_{np}}$ are statistical mean free sliding distances of dislocations in the aluminum alloy under proportional, circle, and other non-proportional loading paths, respectively.

18. A method of predicting a fatigue life of an aluminum alloy under cyclic multiaxial loading, wherein the method comprises:
configuring a computer-based system to predict the fatigue life, the computer-based system comprising:
an information input configured to receive at least one of information relating to the aluminum alloy and information relating to a stress state present in the aluminum alloy and microstructure characteristics and thermophysical and mechanical properties of the aluminum alloy,
an information output configured to convey information relating to the aluminum alloy,
at least one of an information memory and an instruction-storing memory,
a central processing unit, and
computer-readable program code to process the received information relating to aluminum alloy, wherein the received information relating to the aluminum alloy comprises
a hardening factor of the aluminum alloy attributable to cyclic multiaxial loading, the hardening factor defined by at least one of a plurality of uniaxial cyclic hardening factor parameters comprising a fatigue strength coefficient, a fatigue ductility coefficient, a fatigue strength exponent, and a fatigue ductility exponent,
an additional hardening factor due to dislocation interactions in multiple slip systems activated by cyclic multiaxial non-proportional loading, the additional hardening defined by an additional hardening coefficient, a hardening exponent of torsion, and a non-proportionality value, wherein the additional hardening factor parameters are related to probabilistics of microstructure and dislocation structures in the aluminum alloy, and at least one of:
a critical shear plane of the aluminum alloy where a shear strain amplitude is at its maximum value,
a damage factor of the aluminum alloy attributable to cyclic multiaxial loading, the damage factor defined by at least one of a plurality of damage factor parameters comprising a maximum shear strain amplitude, a normal strain amplitude, a maximum normal strain amplitude, a shear stress amplitude, and a normal stress amplitude, and
a characteristic microstructure feature and thermophysical and mechanical properties of the aluminum alloy defined by at least one of a size of a defect, a volume fraction of the defects, secondary dendrite arm spacing (SDAS), a grain size, a size of the second phase particle, an aspect ratio of the second phase particle, a volume fraction of the second phase particles, a shear modulus value a Poisson ratio, and a Young's modulus value;
wherein size distributions of casting defects or microstructure characteristics are determined by an extreme value statistics (EVS) with a cumulative distribution function expressed as:

$$F(x) = \exp\left(-\exp\left(-\frac{x-\zeta}{\delta}\right)\right)$$

where x is a characteristic parameter of casting defects or microstructure characteristics and $\zeta$ and $\delta$ are extreme value statistical distribution parameters; and
predicting the fatigue life of the aluminum alloy with the computer-based system according to processes of the computer-readable program code.

19. The method of claim 18, wherein the fatigue life model comprises a low cycle multiaxial fatigue life model expressed as:

$$\frac{\Delta \gamma_{max}}{2} + \frac{\Delta \varepsilon_n}{2} = \left(\frac{3+v_e}{2}\right)\frac{\sigma'_f}{E}(2N_f)^{b_0} + \left(\frac{3+v_p}{2}\right)(1+L_0\Phi)^{\frac{-1}{n_0}}\varepsilon'_f(2N_f)^{c_0}$$

where ($N_f$) is the fatigue life of the aluminum alloy; $\Delta\gamma_{max}$ is the maximum shear strain amplitude on the critical shear plane; $\Delta\varepsilon_n$ is the normal strain amplitude on the critical shear plane; $v_e$ and $v_p$ are the elastic and plastic Poisson ratios, respectively; E is the Young's modulus value; $L_0$ is the additional hardening coefficient under non-proportional loadings; $n_0$ is the hardening exponent under torsion loading; and $\Phi$ is the non-proportionality value.

20. The method of claim 18, wherein the fatigue life model comprises a high cycle multiaxial fatigue life model expressed as:

$$\frac{\Delta \gamma_{max}}{2} + \frac{\Delta \varepsilon_{max}}{2} = (2+v_e)\frac{\sigma'_f}{E}(2N_f)^{b_0} + (1+L_0\Phi)^{\frac{-1}{n_0}}(2+v_p)\varepsilon'_f(2N_f)^{c_0}$$

where ($N_f$) is the fatigue life of the aluminum alloy; $\Delta\gamma_{max}$ is the maximum shear strain amplitude on the critical shear plane; $\Delta\varepsilon_{max}$ is the maximum normal strain amplitude on the critical shear plane; $v_e$ and $v_p$ are the elastic and plastic Poisson ratios, respectively; E is the Young's modulus value; $L_0$ is the additional hardening coefficient under non-proportional loadings; $n_0$ is the hardening exponent under torsion loading; and $\Phi$ is the non-proportionality value.

21. The method of claim 18, wherein the uniaxial cyclic hardening factor parameters of the hardening factor are related to probabilistics of defects and microstructure characteristics in the aluminum alloy.

22. The method of claim 21, wherein:
the fatigue strength coefficient ($\sigma'_f$) is related to the defect size ($a_i$) in the aluminum alloy through an inverse of a fatigue crack growth Paris law exponent (m);
the fatigue ductility coefficient ($\varepsilon'_f$) is related to a tensile strain hardening exponent (n) that is related to a volume fraction of defects, a volume fraction of second phase particles, secondary dendrite arm spacing (SDAS), and the yield strength of the aluminum alloy such that:

$$\sigma_{YS} + C_1(f_p - f_d)\alpha\varepsilon^* + C_2(1+(f_p-f_d)^{1/2})\left[\left(\frac{C_3}{L}+\frac{C_4}{\lambda}\right)(n-\varepsilon^*)\right]^{1/2} =$$
$$\frac{1}{2}C_2(1+(f_p-f_d)^{1/2})\left(\frac{C_3}{L}+\frac{C_4}{\lambda}\right)^{1/2}(n-\varepsilon^*)^{1/2}$$

where $\sigma_{YS}$ is the yield strength, $C_1$, $C_2$, $C_3$, $C_4$, and L are constants, $\varepsilon^*$ is the strain at the onset of plastic relaxation, $f_p$ and $f_d$ are volume fractions of second phase particles and defects, respectively, and $\lambda$ is an SDAS,
the fatigue strength exponent ($b_0$) is inversely related to the fatigue crack growth Paris law exponent (m) and
the fatigue ductility exponent ($c_0$) is related to the fatigue strength exponent ($b_0$) and inversely related to a tensile strain hardening exponent, (n).

23. An article of manufacture to predict a fatigue life of an aluminum alloy under cyclic multiaxial loading, the article of manufacturing comprising:

a computer-based system to predict the fatigue life, the computer-based system comprising:
an information input configured to receive at least one of information relating to the aluminum alloy and information relating to a stress state present in the aluminum alloy and microstructure characteristics and thermophysical and mechanical properties of the aluminum alloy,
an information output configured to convey information relating to the aluminum alloy,
at least one of an information memory and an instruction-storing memory,
a central processing unit, and
computer-readable program code to process the received information, the received information comprising
a hardening factor of the aluminum alloy attributable to cyclic multiaxial loading, the hardening factor defined by at least one of a plurality of uniaxial cyclic hardening factor parameters comprising a fatigue strength coefficient, a fatigue ductility coefficient, a fatigue strength exponent, and a fatigue ductility exponent,
an additional hardening factor due to dislocation interactions in multiple slip systems activated by cyclic multiaxial non-proportional loading, the additional hardening defined by an additional hardening coefficient, a hardening exponent of torsion, and a non-proportionality value, wherein the additional hardening factor parameters are related to probabilistics of microstructure and dislocation structures in the aluminum alloy, and:
a critical shear plane of the aluminum alloy where a shear strain amplitude is at its maximum value,
a damage factor of the aluminum alloy attributable to cyclic multiaxial loading, the damage factor defined by at least one of a plurality of damage factor parameters comprising a maximum shear strain amplitude, a normal strain amplitude, a maximum normal strain amplitude, a shear stress amplitude, and a normal stress amplitude, and
a characteristic microstructure feature and thermophysical and mechanical property of the aluminum alloy defined by a size of a defect, a volume fraction of the defects, secondary dendrite arm spacing (SDAS), a grain size, a size of the second phase particle, an aspect ratio of the second phase particle, a volume fraction of the second phase particles, a shear modulus value; a Poisson ratio; and a Young's modulus value;
wherein the computer-based system predicts the fatigue life of the aluminum alloy according to processes of the computer-readable program code and;
wherein the computer-readable program code comprises a low cycle multiaxial fatigue life model expressed as:

$$\frac{\Delta \gamma_{max}}{2} + \frac{\Delta \varepsilon_n}{2} = \left(\frac{3+v_e}{2}\right)\frac{\sigma'_f}{E}(2N_f)^{b_0} + \left(\frac{3+v_p}{2}\right)(1+L_0\Phi)^{\frac{-1}{n_0}}\varepsilon'_f(2N_f)^{c_0}$$

where ($N_f$) is the fatigue life of the material; $\Delta\gamma_{max}$ is the maximum shear strain amplitude on the critical shear plane; $\Delta\varepsilon_n$ is the normal strain amplitude on the critical shear plane; $v_e$ and $v_p$ are the elastic and plastic Poisson ratios, respectively; E is the Young's modulus value; $\sigma'_f$ is the fatigue strength coefficient; $\varepsilon'_f$ is the fatigue ductility coefficient; $b_0$ and $c_0$ are the fatigue strength and the fatigue ductility exponents, respectively; $L_0$ is the additional hardening coefficient under non-proportional loadings; $n_0$ is the hardening exponent under torsion loading; and $\Phi$ is the non-proportionality value.

24. The article of manufacture of claim 23, wherein the uniaxial cyclic hardening factor parameters of the hardening factor are related to probabilistics of defects and microstructure characteristics in the aluminum alloy.

25. An article of manufacture to predict a fatigue life of an aluminum alloy under cyclic multiaxial loading, the article of manufacturing comprising:
  a computer-based system to predict the fatigue life, the computer-based system comprising:
    an information input configured to receive at least one of information relating to the aluminum alloy and information relating to a stress state present in the aluminum alloy and microstructure characteristics and thermophysical and mechanical properties of the aluminum alloy,
    an information output configured to convey information relating to the aluminum alloy,
    at least one of an information memory and an instruction-storing memory,
    a central processing unit, and
    computer-readable program code to process the received information, the received information comprising at least one of
      a hardening factor of the aluminum alloy attributable to cyclic multiaxial loading, the hardening factor defined by at least one of a plurality of uniaxial cyclic hardening factor parameters comprising a fatigue strength coefficient, a fatigue ductility coefficient, a fatigue strength exponent, and a fatigue ductility exponent,
      an additional hardening factor due to dislocation interactions in multiple slip systems activated by cyclic multiaxial non-proportional loading, the additional hardening defined by an additional hardening coefficient, a hardening exponent of torsion, and a non-proportionality value, wherein the additional hardening factor parameters are related to probabilistics of microstructure and dislocation structures in the aluminum alloy, and at least one of:
      a critical shear plane of the aluminum alloy where a shear strain amplitude is at its maximum value,
      a damage factor of the aluminum alloy attributable to cyclic multiaxial loading, the damage factor defined by at least one of a plurality of damage factor parameters comprising a maximum shear strain amplitude, a normal strain amplitude, a maximum normal strain amplitude, a shear stress amplitude, and a normal stress amplitude, and
      a characteristic microstructure feature and thermophysical and mechanical property of the aluminum alloy defined by a size of a defect, a volume fraction of the defects, secondary dendrite arm spacing (SDAS), a grain size, a size of the second phase particle, an aspect ratio of the second phase particle, a volume fraction of the second phase particles, a shear modulus value; a Poisson ratio; and a Young's modulus value;
    wherein the computer-based system predicts the fatigue life of the aluminum alloy according to processes of the computer-readable program code; and
    wherein the computer-readable program code comprises a high cycle multiaxial fatigue life model expressed as:

$$\frac{\Delta \gamma_{max}}{2} + \frac{\Delta \varepsilon_{max}}{2} = (2+v_e)\frac{\sigma'_f}{E}(2N_f)^{b_0} + (1+L_0\Phi)^{\frac{-1}{n_0}}(2+v_p)\varepsilon'_f(2N_f)^{c_0}$$

where ($N_f$) is the fatigue life of the material; $\Delta\gamma_{max}$ is the maximum shear strain amplitude on the critical shear plane; $\Delta\varepsilon_{max}$ is the maximum normal strain amplitude on the critical shear plane; $v_e$ and $v_p$ are the elastic and plastic Poisson ratios, respectively; E is the Young's modulus value; $\sigma'_f$ is the fatigue strength coefficient; $\varepsilon'_f$ is the fatigue ductility coefficient; $b_0$ and $c_0$ are the fatigue strength and the fatigue ductility exponents, respectively; $L_0$ is the additional hardening coefficient under non-proportional loadings; $n_0$ is the hardening exponent under torsion loading; and $\Phi$ is the non-proportionality value.

26. The article of manufacture of claim 25, wherein the uniaxial cyclic hardening factor parameters of the hardening factor are related to probabilistics of defects and microstructure characteristics in the aluminum alloy.

* * * * *